United States Patent
Marra

(10) Patent No.: US 8,701,466 B2
(45) Date of Patent: Apr. 22, 2014

(54) DEVICE FOR CHARACTERIZING THE EVOLUTION OVER TIME OF A SIZE DISTRIBUTION OF ELECTRICALLY-CHARGED AIRBORNE PARTICLES IN AN AIRFLOW

(75) Inventor: Johan Marra, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 160 days.

(21) Appl. No.: 13/126,037

(22) PCT Filed: Oct. 26, 2009

(86) PCT No.: PCT/IB2009/054716
§ 371 (c)(1),
(2), (4) Date: Apr. 26, 2011

(87) PCT Pub. No.: WO2010/049870
PCT Pub. Date: May 6, 2010

(65) Prior Publication Data
US 2011/0197656 A1    Aug. 18, 2011

(30) Foreign Application Priority Data
Oct. 31, 2008 (EP) .................................. 08168053

(51) Int. Cl.
*G01N 37/00* (2006.01)
(52) U.S. Cl.
USPC ....................................................... 73/28.02
(58) Field of Classification Search
USPC ....................................................... 73/28.02
See application file for complete search history.

(56) References Cited

FOREIGN PATENT DOCUMENTS

| GB | 2195204 A | | 3/1988 |
|---|---|---|---|
| GB | 2371362 A | * | 7/2002 |
| WO | WO2007000710 A2 | | 1/2007 |

* cited by examiner

*Primary Examiner* — R. A. Smith
*Assistant Examiner* — Alex Devito
(74) *Attorney, Agent, or Firm* — Larry Liberchuk

(57) ABSTRACT

A device is presented that is capable of recording the evolution over time of the characteristics of a size distribution of electrically-charged airborne particles in an airflow. The device comprises an air inlet, a particle charging unit, a concentration variation section, a particle sensing section and a data evaluation unit. Specifically, the particle sensing section of the device generates at least two serially obtained measurement signals $I_1$ and $I_2$ from which the data evaluation unit can infer values for both the average particle diameter $d_{p,av}$ and the number concentration N of the size distribution of electrically-charged airborne particles. Reliable values can be obtained for N and $d_{p,av}$ under both stationary conditions and transient conditions with respect to the characteristics of the particle size distribution due to the condition that the change of the inferred average particle diameter $d_{p,av}$ with respect to a reference particle diameter $d_{p,ref}$ is bounded by a set maximum change. This imposed condition markedly reduces scatter in the inferred values for dp,av and N as a function of time, while still allowing transient characteristics with respect to both N and $d_{p,av}$ to become visible in the course of time, without having to rely on averaging procedures and/or device hardware adaptations.

13 Claims, 2 Drawing Sheets

DEVICE FOR CHARACTERIZING THE EVOLUTION OVER TIME OF A SIZE DISTRIBUTION OF ELECTRICALLY-CHARGED AIRBORNE PARTICLES IN AN AIRFLOW

FIELD OF THE INVENTION

The present invention generally relates to a device for characterizing the evolution over time of a size distribution of electrically-charged airborne particles in an airflow.

BACKGROUND OF THE INVENTION

The air around us contains particles of different sizes and shapes, which together with exhaust gasses and other contaminations contribute to the total air pollution in an area. Some of the particles are man-made and may originate from e.g the burning of fossil fuels in vehicles. Others occur naturally and may originate from volcanoes, dust storms, forest fires etc. Particles within the 5-500 nm size range are classified as ultrafine particles (UFPs). UFPs, like for instance soot particles, are known to be particularly health-hazardous to humans. It has been verified that inhalation of airborne UFPs can result in severe lung injuries due to their deposition in the lungs.

In view of the above, the measuring of the characteristics of UFPs in the air around us is of great importance. Information regarding the characteristics of airborne ultrafine particles (UFPs) may be collected using a UFP measuring device which enables a local detection of airborne particles and involves the measuring of the particle number concentration N, the number-averaged particle diameter $d_{p,av}$, and the particle size distribution $dN(d_p)/d\ln(d_p)$ in the air. Specifically, the incurred health-hazard associated with exposure to UFP air pollution is believed to relate to the UFP length concentration $L=N*d_{p,av}$. The reason for the latter inference comes from the consideration (see, for example, H. Fissan et. al., Journal of Nanoparticle Research (2007), Vol. 9, pp. 53-59) that the relative health-hazard of inhaled airborne particles is likely to be associated with the particle surface area per unit volume of inhaled air that deposits in the respiratory tract following inhalation. In addition, this deposited particle surface area concentration can be shown to be proportional with the particle length concentration L in the inhaled air when the deposition efficiency of inhaled airborne particles as a function of their diameter in the various regions of the respiratory tract is properly accounted for (International Commission for Radiological Protection, ICRP, 1994).

A prior art UFP sensor disclosed in WO2007/000710 A2 is illustrated in FIG. 1a. The measuring device 10 comprises an air inlet section 11 which is optionally provided with a particle prefilter 12. The UFP sensor further comprises a particle charging section 18 capable of electrically charging airborne particles in the sampled airflow after their entry into the device 10. In addition, the UFP sensor 10 comprises a particle sensing section 13 comprising a Faraday cage arrangement 16, which is electrically insulated from the remainder of the UFP sensor 10, and which is connected via a sensitive current meter 15 to earth potential. Electrically charged particles in the airflow entering the Faraday cage arrangement 16 are captured by an air-permeable filtration medium inside the Faraday cage together with their charge, thereby giving rise to an electrical current $I_s$, which is measurable by the current meter 15, that is equal to the electrical charge deposited per unit time inside the Faraday cage arrangement 16. The magnitude of the current $I_s$ has a proportionality to the concentration level of airborne electrically-charged UFPs in the airflow entering the Faraday cage arrangement 16, the proportionality factor being determined by the average electrical charge on the airborne particles. In case particle charging in the charging section 18 is accomplished by diffusion charging, $I_s$ is proportional to the particle length concentration $L=N*d_{p,av}$ (M. Adachi et. al., Journal of Aerosol Sci. 16(2), pp. 109-123, 1985).

The UFP sensor in FIG. 1a is further arranged with a particle concentration variation section 17, arranged downstream from the particle charging section 18, which is capable of causing a variation of the concentration of electrically-charged UFPs between a first concentration level and a second concentration level. In FIG. 1a, the concentration variation section 17 is embodied as a parallel-plate section (also referred to as "plate section") comprising an air conduit 19 formed by parallel-plate electrode surfaces between which an electric potential difference $V_p$ can be applied. An electric potential difference between the electrode plates creates an electric field across the conduit 19. In case no electric field is applied across the conduit, the concentration level of airborne electrically-charged particles exiting the plate section (the first concentration level) will be substantially the same as the concentration level of airborne electrically-charged particles entering the plate section. In case a non-zero electric field is applied between the plates across the conduit, at least part of the airborne electrically-charged particles entering the plate section will be electrostatically precipitated onto one of the electrode surfaces, thereby reducing the concentration level of the airborne electrically-charged particles exiting the plate section to a smaller second concentration level. The concentration level of electrically-charged particles exiting the plate section is subsequently received by the Faraday cage arrangement 16, giving rise to a sensor current $I_s$ that is measured by the current meter 15.

As described above, the magnitude of the measured electrical current signal $I_s$ is proportional to the concentration level of electrically-charged UFPs in the airflow received by the Faraday cage arrangement 16 and varies when the concentration level of the electrically-charged UFPs varies. In response to an applied particle concentration variation in the course of time, the known sensor 10 determines measurement signals associated with varied particle concentration levels in a serial way during successive time intervals. A set comprising at least two measurement signals corresponding with a set of at least two varied particle concentration levels is required and sufficient for determining the total particle number concentration N and the average particle diameter $d_{p,av}$. Different sets of measurement signals can be successively determined to follow the evolution of the total particle number concentration and the average particle diameter in the course of time.

For an accurate determination of the total particle number concentration N and the average particle diameter $d_{p,av}$ of airborne particles, the known sensor 10 requires an environment wherein the total concentration of airborne particles and the particle size distribution (i.e. the particle concentration as a function of particle size) should be no more than only a slowly varying function of time, preferably substantially stationary in time. During the time interval required to measure a single set of two serially obtained measurement signals, as required for a single determination of the total particle number concentration and the average particle diameter, the total particle number concentration and the average particle diameter should remain substantially constant.

This time interval cannot be made arbitrarily small because of minimum required demands on the measurement accuracy that normally necessitate signal averaging during at least a minimum period of time. For accurate operation in a non-stationary transient environment, a device is required that can determine the total particle number concentration N and the average particle diameter $d_{p,av}$ of airborne particles also under highly transient conditions wherein the particle concentration level may rapidly change during the course of time. Such circumstances can for instance arise at or near a location where motorized traffic is present.

In the prior art, and as described above, the particle number concentration N and the average diameter $d_{p,av}$ of airborne particles are inferred from a serial measurement of 2 successively recorded sensor signals $I_s$, one signal $I_s=I_1$ being measured at a precipitation voltage $V_p=0$ in the plate section, the other signal $I_s=I_2$ being measured at a precipitation voltage $V_p=V_1$ (see FIG. 1b)). Because an applied non-zero $V_p=V_1$ removes at least part of the electrically-charged particles from the airflow passing through the plate section 17, one will normally have $I_2<I_1$.

It is instructive to briefly describe the relative accuracy with which N and $d_{p,av}$ can be inferred with the device 10 from the measured signals $I_1$ and $I_2$ under stationary conditions wherein the characteristics of the size distribution of the electrically-charged airborne particles remain substantially constant in the course of time. At an airflow $\phi$ (m³/s) through the sensor, relative to a reference airflow $\phi^*$ through a proportionally differently sized sensor (the sensor size and the airflow $\phi$ being related to each other in such a way that the air velocities inside the sensor remain substantially constant and independent of $\phi$), N relates to $I_1$ and $I_2$ according to Eq. 1:

$$N = S_N \frac{\phi^*}{\phi}(I_1 - I_2) \text{ (particles/cm}^3\text{)} \quad \text{Eq. 1}$$

with $S_N$ a first proportionality constant. $d_{p,av}$ relates to $I_1$ and $I_2$ according to Eq. 2:

$$d_{p,av} = S_{dp}\frac{I_1}{I_1 - I_2} \text{ (nm)} \quad \text{Eq. 2}$$

with $S_{dp}$ a second proportionality constant. Finally, the particle length concentration L relates to only $I_1$ according to Eq. 3:

$$L = Nd_{p,av} = S_N S_{dp} I_1 \text{ ((particles/cm}^3\text{)·nm)} \quad \text{Eq. 3}$$

Under stationary conditions with respect to N and $d_{p,av}$, the relative inaccuracies $\Delta N/N$ and $\Delta d_{p,av}/d_{p,av}$ can be shown to relate to the measurement inaccuracy $\Delta I_s$ of the sensor signal $I_s$ according to Eqs. 4 and 5, respectively:

$$\frac{\Delta N}{N} = \frac{2S_N}{N}\frac{\phi^*}{\phi}\Delta I_s \quad \text{Eq. 4}$$

$$\frac{\Delta d_{p,av}}{d_{p,av}} = \frac{\Delta I_s}{I_1} + \frac{2\Delta I_s}{I_1 - I_2}$$

$$= \frac{\phi^*}{\phi}\frac{\Delta I_s}{N}\left(\frac{S_N S_{dp}}{d_{p,av}} + 2S_N\right)$$

$\Delta I_S$ is about $1*10^{-15}$ A (=1 fA) for the best operational amplifiers that are currently on the market and cannot easily be made smaller because of electronic noise. This circumstance sets a limit to the attainable accuracy of a single determination of N and $d_{p,av}$. In addition, the relative uncertainties $\Delta N/N$ and $\Delta d_{p,av}/d_{p,av}$ increase at smaller values for N and/or $\phi$. The airflow $\phi$ can be increased to reduce the relative uncertainties/inaccuracies but this cannot generally be done without increasing the sensor size. This increase is undesirable because people normally wish the sensor size to remain as small as possible, also from the point of view of cost and portability. Similarly, a reduction in the sensor size will reduce $\phi$, thereby increasing the relative uncertainties $\Delta N/N$ and $\Delta d_{p,av}/d_{p,av}$. This increases the scatter in the inferred values of N and $d_{p,av}$ as a function of time. As long as the air pollution characteristics in terms of N and $d_{p,av}$ remain substantially constant in time, an improved degree of accuracy and thus reliability can be accomplished, also at a relatively small value for $\phi$, by averaging the outcomes of successively obtained measurements in the course of time. This averaging can be done either with regard to the measured $I_1$ and $I_2$ signals, or with regard to the inferred values N and $d_{p,av}$ from these signals.

The approach of averaging several serially obtained measurements cannot be used when the air pollution characteristics in terms of N and $d_{p,av}$ change in the course of time (i.e. when they become transient). This is particularly so because the sensor signals $I_1$ and $I_2$ are obtained serially in time when the set-up depicted in FIG. 1a is used. When rapid changes in the air pollution characteristics occur, the successively obtained signals $I_1$ and $I_2$ are recorded under different air pollution conditions and can therefore not reliably be combined together in Eqs. 1-3 for inferring N and $d_{p,av}$, thereby greatly increasing the relative inaccuracies $\Delta N/N$ and $\Delta d_{p,av}/d_{p,av}$.

It is quite possible that at some stage $I_1<I_2$, which gives a nonsense outcome w.r.t. N and $d_{p,av}$ when Eqs. 1-3 are used. A separate averaging of the serially measured currents $I_1$ and $I_2$ over a certain period of time provides no solution to improve upon this situation because this only tends to dampen the observed air pollution transients that one just wants to measure. Strictly speaking, Eqs. 1 and 2 lose their validity when the serially measured sensor signals $I_1$ and $I_2$ are obtained under different (transient) conditions with respect to the particulate air pollution characteristics. Reliable data for N and $d_{p,av}$, inferred from the signals $I_1$ and $I_2$ according to Eqs. 1-3, can then not anymore be obtained in the course of time.

SUMMARY OF THE INVENTION

In view of the above, it would be desirable to achieve an improved device and method for inferring the characteristics of the size distribution of airborne ultrafine particles in the course of time which at least alleviates the above mentioned problems with the prior art.

According to a first aspect of the present invention there has been provided a device for characterizing the evolution over time of a size distribution of electrically-charged airborne particles in an airflow, comprising:

an air inlet for entry of airborne particles in an airflow, a particle charging unit arranged to create the size distribution of electrically-charged airborne particles by electrically charging airborne particles entering the device, a concentration variation section capable of causing a variation of the concentration of electrically-charged particles between at least a first concentration level and a second concentration level during at least one time interval, a particle sensing section capable of producing a first measurement signal $I_1$ corresponding with the first concentration level, and a second measurement signal $I_2$ corresponding with the second concentration level, and a data evaluation unit being arranged to infer, from the first measurement signal $I_1$ and the second measurement signal $I_2$ and a reference particle diameter $d_{p,ref}$, a particle number concentration N and an average particle diameter $d_{p,av}$ of the size distribution of electrically-charged airborne particles. The change of the inferred average particle diameter $d_{p,av}$ with respect to the reference particle diameter $d_{p,ref}$ is bounded by a set maximum change.

Thus, there is provided a device arranged to follow the potentially transient characteristics N and $d_{p,av}$ for a size distribution of airborne particles, e.g. UFPs, in an airflow in the course of time. The device is arranged such that when evaluating the measurement signals $I_1$ and $I_2$ for inferring the particle concentration N and the average particle diameter $d_{p,av}$, restrictions are set on the allowed change of the inferred average particle diameter with respect to a reference particle diameter $d_{p,ref}$. More particularly, the change is bounded by a set maximum change. This restriction is physically reasonable because, with a given pollution source that produces the particulate air pollution, a transient in the characteristics of the particle size distribution usually relates relatively more to a transient in the particle number concentration than to a transient in the average particle diameter. The circumstance to allow at most only a limited change in $d_{p,av}$ with respect to a reference particle diameter does allow $d_{p,av}$ to undergo changes in the course of time, yet reduces the deviation in the inferred value for $d_{p,av}$ with respect to $d_{p,ref}$ and ensures the inferred $d_{p,av}$ to remain physically realistic under a wide variety of conditions when $d_{p,ref}$ is a judiciously chosen physically-realistic average particle diameter. No limitations are imposed in as far as the values for N and the changes therein are concerned. This improves the overall reliability and reduces the scatter over time with respect to the inferred values for N and $d_{p,av}$ without having to rely on hardware adaptations or averaging procedures. The improved accuracy not only applies to the inferred values for N and $d_{p,av}$ obtained under transient conditions but also under stationary conditions when N and/or φ is relatively low. According to Eq. 1, a small particle number concentration N is accompanied by only a small value for the signal difference $(I_1-I_2)$ and thus a relative large uncertainty in the inferred value for $d_{p,av}$ according to Eq. 2, wherein $(I_1-I_2)$ shows up in the denominator.

In accordance with an embodiment of the device, the particle number concentration N is inferred on the basis of the first measurement signal $I_1$, the second measurement signal $I_2$, and the inferred average particle diameter $d_{p,av}$ of the size distribution of electrically-charged airborne particles. This procedure ensures internal consistency of the inferred values for N and $d_{p,av}$ with respect to the measured signals $I_1$ and $I_2$, thereby yielding a physically realistic result not only for $d_{p,av}$ but also for N without having to rely on averaging procedures or on restrictions with respect to the change in the inferred values for N in the course of time.

In accordance with an embodiment of the device, the concentration variation section is an electrical precipitation unit capable of electrically precipitating at least part of the size distribution of electrically-charged airborne particles during at least one time interval. This embodiment enables a convenient and controllable way of varying the concentration of the size distribution of electrically-charged airborne particles by means of applying an electric field across the flow conduit located between two parallel electrode surfaces inside the precipitation unit, as described before for the prior art device 10 in FIG. 1a. The electric field is preferably chosen such as to only precipitate part of the electrically-charged particles of any given size that contribute to a non-negligible extent to the total particle number concentration N. More in particular, the applied electric field across the flow conduit is chosen such that electrically-charged particles larger than 10 nm in diameter are only partially precipitated from the airflow passing through the precipitation unit.

In accordance with an embodiment of the device, the first concentration level is substantially the same as the concentration level of the created size distribution of electrically-charged airborne particles. This is advantageous as it allows the measured signal $I_1$ to correspond with the characteristics of the created size distribution of electrically-charged airborne particles inside the sensor device following the electric charging of the airborne particles entering the sensor device. Preferably, charging of the airborne particles inside the charging section of the sensor device is accomplished with diffusion charging. The signal $I_2$ can subsequently be made to correspond to the characteristics of the size distribution of electrically-charged airborne particles that is obtained after the concentration of the initially created size distribution of electrically-charged airborne particles has been reduced by means of a partial electrostatic particle precipitation inside the precipitation section of the sensor device. This procedure allows the use of Eqs. 1-3 to infer the characteristics of the initially created size distribution of electrically-charged airborne particles from the signals $I_1$ and $I_2$.

In accordance with an embodiment of the device, the reference particle diameter $d_{p,ref}$ is a pre-defined particle diameter $d_{p,0}$. The pre-defined particle diameter corresponds to a default value of the particle diameter, which may be set by the user of the device, and which preferably represents an approximately expected average particle diameter. Specifically, use of a pre-defined particle diameter $d_{p,0}$ as a reference particle diameter is advantageous when the first signals $I_1$ and $I_2$ are recorded immediately after the sensor device has been switched on. No previously inferred values for $d_{p,av}$ are then available, and it is then preferred to rely on the value of the pre-defined particle diameter $d_{p,0}$ in order to ensure that no physically unrealistic values for $d_{p,av}$ and N are inferred from $I_1$ and $I_2$ in case the size distribution of electrically-charged airborne particles exhibits a transient behavior in its characteristics during the time when the first signals $I_1$ and $I_2$ are recorded immediately after the sensor device has been switched on.

In accordance with an embodiment of the device, the pre-defined particle diameter $d_{p,0}$ is preferably set at a value within the 20-100 nm size range, which is a typical size range for the number-averaged particle diameter of airborne ultrafine particles sized between approximately 10 and 300 nm.

In accordance with an embodiment of the device, the reference particle diameter $d_{p,ref}$ is a previously inferred particle diameter, preferably the most recently inferred previous value for $d_{p,av}$. This increases the accuracy and reliability of the inferred values for $d_{p,av}$ and N at any given moment in time, because it is not normally expected that major changes in $d_{p,av}$ will occur within the brief period of time between successive recordings of the signals $I_1$ and $I_2$. A controlled gradual change in successively inferred values for $d_{p,av}$ is now allowed, involving only a minimum amount of history with respect to the previously inferred values for $d_{p,av}$, the history being preferably formed by a single number for $d_{p,ref}$ set equal to the most recently inferred previous value of $d_{p,av}$.

In accordance with an embodiment of the device, the inferred average particle diameter $d_{p,av}$ is taken to be equal to the reference particle diameter $d_{p,ref}$, the value for $d_{p,ref}$ preferably representing the most recently inferred value for $d_{p,av}$ or a pre-defined value $d_{p,0}$, when $I_1 \leq I_2$ or when $I_1$ is smaller than or equal to a pre-defined reference signal $I_{1,ref}$. When $I_1 \leq I_2$, $d_{p,av}$ cannot be inferred from Eq. 2 as this would lead to a physically unrealistic negative value for $d_{p,av}$. The circumstance that $I_1 \leq I_2$ may occur under highly transient conditions with respect to the characteristics of the size distribution of airborne electrically-charged particles or when the magnitudes of the signals $I_1$ and $I_2$ are too small to be recorded with a satisfactory degree of accuracy. The circumstance that $I_1 \leq I_{1,ref}$, with the magnitude of $I_{1,ref}$ preferably representing a value that is either zero or a value close to zero (preferably in the 0-10 fA range), may occur at relatively small particle concentrations N that give rise to the measurement of signals $I_1$ and $I_2$ that are too small to be recorded with a satisfactory degree of accuracy and that are therefore not suitable to infer reliable values for $d_{p,av}$ according to Eq. 2, even when $I_1 > I_2$.

In accordance with an embodiment of the device, the mathematical product $N^*d_{p,av}$ of the inferred average particle diameter $d_{p,av}$ and the inferred particle number concentration N is set to be proportional to the first measurement signal $I_1$. This is in accordance with Eq. 3 and ensures under all circumstances that the inferred values of N and $d_{p,av}$ are related to each other in such a way that their product L is proportional to $I_1$. This is physically justified following the observation that $L \propto I_1$ when particle charging is accomplished by means of diffusion charging (M. Adachi et. al., Journal of Aerosol Sci. 16(2), pp. 109-123, 1985).

In turn, as discussed before, L is believed to be proportional to the exposure-related health-hazard when inhaling air that is polluted with the size distribution of airborne particles. This procedure ensures that under all conditions and circumstances, a reliable assessment of the exposure-related health-hazard can be obtained via the combined inferred values for N and $d_{p,av}$, or, even more directly, via $I_1$.

In accordance with an embodiment of the device, the set maximum change of the inferred average particle diameter with respect to a reference particle diameter is made dependent on the magnitude of at least one of the two measurements signals $I_1$ and $I_2$. This is advantageous as this condition allows more flexibility in the allowed maximum change of $d_{p,av}$ when successively inferred values for $d_{p,av}$ are compared. At high values for both $I_1$ and $I_2$, the inaccuracies in $I_1$ and $I_2$ are relatively less than when low values for $I_1$ and $I_2$ are recorded, thereby allowing a relative higher value to be used for the set maximum change. This circumstance facilitates also relatively fast transients in $d_{p,av}$ to be recorded over time when these are present. In case a low airborne particle concentration is encountered, small values for $I_1$ and $I_2$ will be measured, which increases the relative uncertainty in the inferred value for $d_{p,av}$ according to Eq. 2. The latter situation can be improved upon by restricting the set maximum change to a relatively smaller value.

In accordance with an embodiment of the device, a series of first measurement signals $I_1(t_k)$, $I_1(t_{k+2})$, $I_1(t_{k+4})$, . . . and a series of second measurement signals $I_2(t_{k+1})$, $I_2(t_{k+3})$, $I_2(t_{k+5})$, . . . are serially produced at successive moments $t_k$, $t_{k+1}$, $t_{k+2}$, . . . in time, with k representing an integer number, and wherein the data evaluation unit is arranged to infer a particle number concentration N and an average particle diameter $d_{p,av}$ of the size distribution of electrically-charged airborne particles at each moment $t_k$, $t_{k+1}$, $t_{k+2}$, . . . when either a first measurement signal $I_1$ or a second measurement signal $I_2$ is produced. This is advantageous since this allows a rapid update of both N and $d_{p,av}$ at each moment in time when either a signal or a signal $I_2$ is recorded.

In accordance with an embodiment of the device, the device is specifically arranged to enable the detection of the evolution over time of the characteristics of a size distribution of electrically-charged airborne particles, which are predominantly electrically-charged ultrafine particles with a diameter in the 5-500 nm size range, more preferably in the 10-300 size range. This is advantageous since these ultrafine particles often represent the most hazardous constituent of the overall encountered air pollution with particles and gases.

The different features of the above-mentioned aspects of the invention can be combined in any combination.

An advantage with the present invention is that a device and method is disclosed that significantly reduces the scatter in the inferred data for $d_{p,av}$ and N in the course of time when using the basic sensor described in WO2007000710 A2 (see FIG. 1a), both when this sensor is used under static conditions and under transient conditions with respect to the particulate air pollution characteristics. This furthermore permits a relatively reduction in both the sensor size and the sensor price (complexity) to be achieved without the trouble of suffering from extra unreliability/scatter in the measurements.

Other objectives, features and advantages of the present invention will appear from the following detailed disclosure, from the attached dependent claims as well as from the drawings.

Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of the element, device, component, means, step, etc., unless explicitly stated otherwise. The steps of any method disclosed herein do not have to be performed in the exact order disclosed, unless explicitly stated.

Unless otherwise defined, all terms (including technical and scientific terms) used herein have the same meaning as commonly understood by one of ordinary skill in the art to which embodiments of the present invention belong. It will be further understood that terms used herein should be interpreted as having a meaning that is consistent with their meaning in the context of this specification and the relevant art and will not be interpreted in an idealized or overly formal sense unless expressly so defined herein.

BRIEF DESCRIPTION OF THE DRAWINGS

Embodiments of the present invention will now be described in more detail, reference being made to the enclosed drawings, in which.

It should be noted that these figures are diagrammatic and not drawn to scale. For the sake of clarity and convenience, relative dimensions and proportions of parts of these figures have been shown exaggerated or reduced in size.

DETAILED DESCRIPTION OF THE EMBODIMENTS

Embodiments of the present invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the detailed description.

The invention is based on the consideration that under virtually all ambient environmental conditions, both indoors and outdoors, large fluctuations in the values for $d_{p,av}$ (i.e. more than about 5-10% within a time span of about 10 seconds) will not normally occur. On the other hand, significant fluctuations in N can certainly occur within a time span of a few seconds and must be duly accounted for.

Figure 1A:
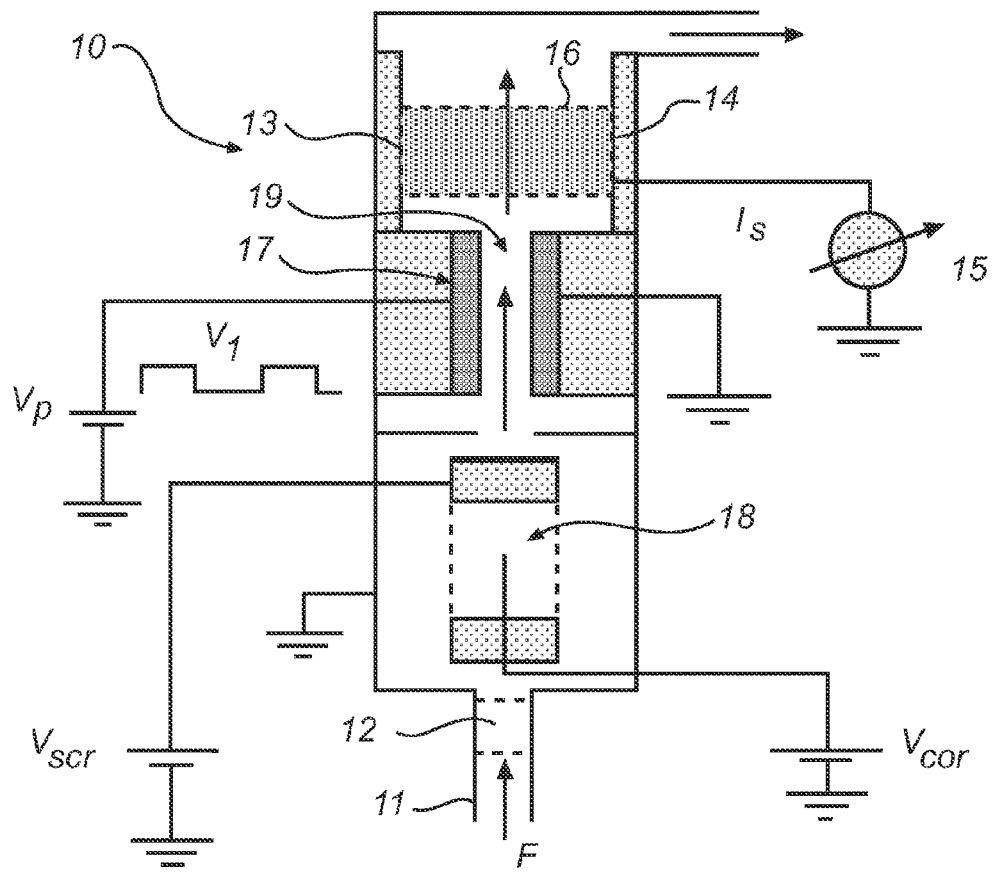
FIGS. 1a and 1b are schematic illustrations of a prior art ultrafine particle sensor.
Figure 1B:
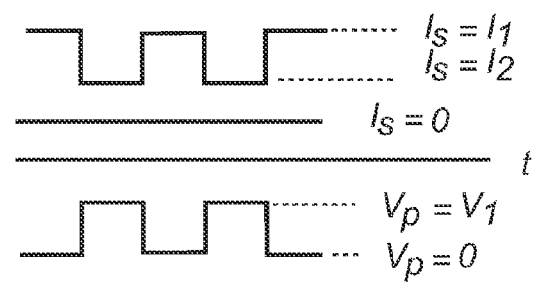
Figure 2:
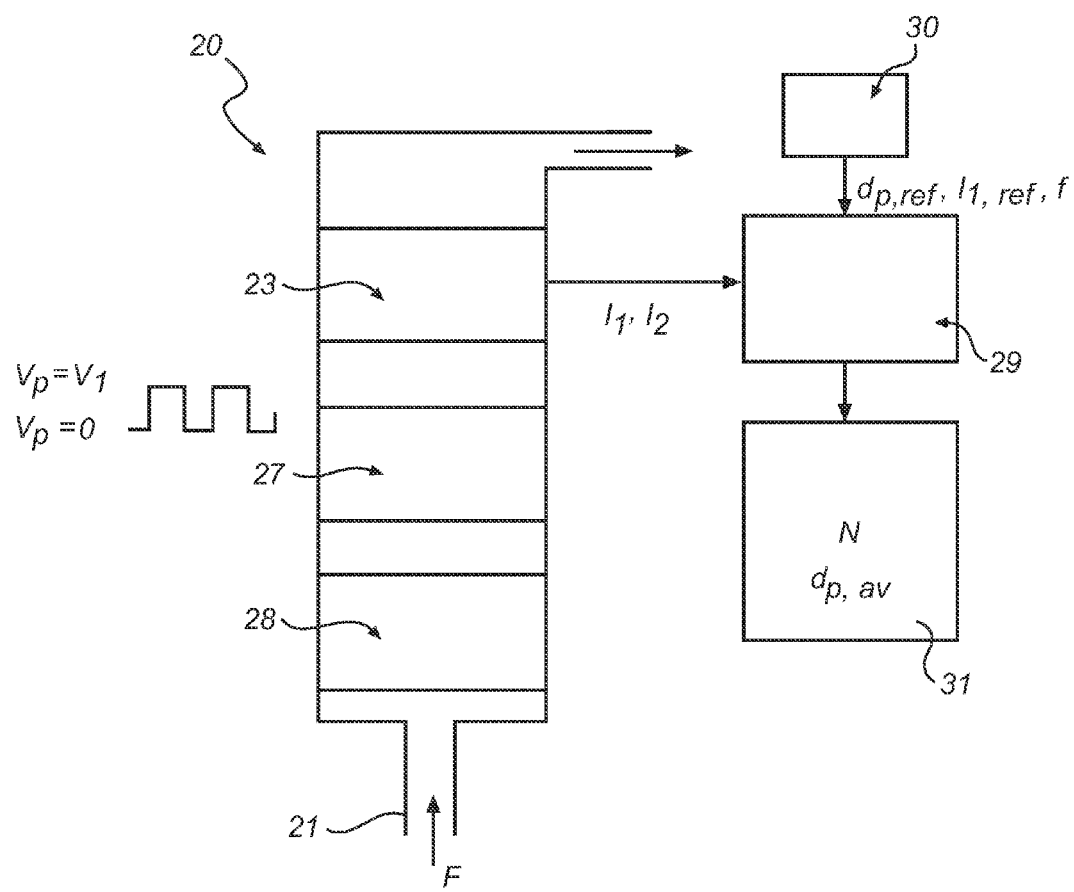
FIG. 2 is a block diagram for a device for characterizing the evolution over time of a size distribution of electrically-charged airborne particles according to an embodiment of the present invention.

Referring now to FIG. 2, an embodiment of a device 20 for characterizing the evolution over time of a size distribution of electrically-charged airborne particles in an airflow is arranged having an air inlet 21 for entry of airborne particles in an airflow F. The airflow F passing through the device 20 can be created by means of a ventilator or a pump (not shown). Further, a particle charging unit 28 is arranged downstream of the air inlet 21 to create the size distribution of electrically-charged airborne particles by electrically charging airborne particles entering the device 20. The charging unit 28 may comprise a needle-tip electrode connected to a high-voltage power supply (comparable to the charging unit 18 in FIG. 1a), which needle electrode is set at an electric potential $V_{cor}$ that is sufficiently high to ionize the air near the needle tip, thereby producing airborne ions that partly adsorb on airborne particles passing through the charging unit 28, thus creating an electrical charge on the airborne particles. Preferably, the needle tip electrode is surrounded by a porous screen electrode set at a screen voltage $V_{scr} \ll V_{cor}$. This enables conditions in the charging unit 28 that are appropriate for realizing diffusion charging of airborne particles. Alternatively, particle charging can be realized by means of photo-ionization through the use of a light source, e.g. a UV lamp or an excimer light source, capable of emitting radiation that comprises sufficiently energetic photons to ionize the airborne particles.

The device 20 is further arranged with a concentration variation section 27, which is arranged downstream from the particle charging unit 28. The concentration variation unit 27 is arranged to be capable of causing a variation of the concentration of electrically-charged particles in the airflow between at least a first concentration level and a second concentration level during at least one time interval. The concentration variation unit 27 is arranged to accomplish the concentration variation by subjecting the airflow comprising charged particles to different electrostatic fields.

In particular, in one embodiment of the device according the present invention, the concentration variation unit 27 is an electrical precipitation unit (comparable to the concentration variation unit 17 as illustrated in FIG. 1a). The concentration variation 27 unit is capable of electrically precipitating at least part of the size distribution of electrically-charged airborne particles during at least one time interval, and may be arranged to comprise a series of straight or cylindrical concentric parallel plates (not shown), of which at least one plate is capable of receiving a periodic series of voltage pulses $V_p = V_1$ while the other plate is continuously connected to a voltage $V_p = 0$. One of the plates is then connected to alternating voltages $V_p = 0$ and $V_p = V_1$, which results in a first concentration level and a second concentration level of electrically-charged airborne particles exiting from the concentration variation section in direct association with the applied voltages $V_p = 0$ and $V_p = V_1$, respectively. Because at least part of the electrically-charged airborne particles will precipitate inside the precipitation unit 27 when a voltage $V_p = V_1$ is applied to one of the plates, the second concentration level is lower than the first level (which is associated with having both plates connected to $V_p = 0$). In this embodiment of the device according to the present invention, the first concentration level is substantially the same as the concentration level of the created size distribution of electrically-charged airborne particles which exits from the particle charging unit 28.

A particle sensing section 23 is located downstream from the concentration variation section 27. The charged particles exiting from the concentration variation section 27 are received by the particle sensing section 23, which is capable of producing a first measurement signal $I_1$ corresponding with the first concentration level, and a second measurement signal $I_2$ corresponding with the second concentration level. The measurement signals may be obtained by utilizing the Faraday cage arrangement connected to a sensitive current meter as shown in FIG. 1a.

The particle sensing section 23 is arranged to communicate with a data evaluation unit 29. The data evaluation unit 29 is capable of receiving input data in the form of measured signals from the particle sensing section 23 and possesses a memory functionality. Optionally, it is arranged with a user interface comprising a data input unit 30 to receive parameters required for enabling the inferring of characteristic data with respect to the size distribution of airborne electrically-charged particles, and a display unit 31 for presenting results to a user. The data evaluation unit 29 is further arranged to infer, from the first measurement signal $I_1$ and the second measurement signal $I_2$ and a reference particle diameter $d_{p,ref}$, a particle number concentration N and an average particle diameter $d_{p,av}$ of the size distribution of electrically-charged airborne particles. The change of the inferred average particle diameter $d_{p,av}$ with respect to the reference particle diameter $d_{p,ref}$ is bounded by a set maximum change which is represented by the numerical value of a parameter f. In addition, a minimum value $I_{1,ref}$ for the first measurement signal $I_1$ may be defined, which is advantageous for making the inferring procedure of N and $d_{p,av}$ from the signals $I_1$ and $I_2$ dependent on the numerical value of $I_1$ and thus on the relative accuracy of $I_1$.

In an embodiment of the device according to the present invention, the reference particle diameter $d_{p,ref}$ is a previously inferred average particle diameter, preferably the previous most recently inferred average particle diameter. In another embodiment of the device according to the present invention, the reference particle diameter $d_{p,ref}$ is a pre-defined particle diameter $d_{p,0}$. Use of the pre-defined particle diameter $d_{p,0}$ for the reference particle diameter $d_{p,ref}$ is particularly advantageous when the first measurements $I_1$ and $I_2$ are obtained immediately after the device has been switched on, since no previously inferred average particle diameter is then available.

In an embodiment of the device according to the present invention, the particle number concentration N is inferred on the basis of the first measurement signal $I_1$, the second measurement signal $I_2$, and the inferred average particle diameter $d_{p,av}$ of the size distribution of electrically-charged airborne particles. The procedure to infer N after having inferred a value for $d_{p,av}$ on the basis of the measured signals $I_1$ and $I_2$ is possible because the mathematical product $N^* d_{p,av}$ is proportional to $I_1$ under conditions of diffusion charging (see Eq. 3). Thus, when both $I_1$ and $d_{p,av}$ are known, it becomes possible to infer N.

According to an embodiment of the device according to the present invention, the device is arranged to characterize electrically-charged airborne particles, which are predominantly electrically-charged ultrafine particles with a diameter in the 5-500 nm size range, more preferably in the 10-300 size range.

According to an embodiment of the invention, a series of first measurement signals $I_1(t_k)$, $I_1(t_{k+2})$, $I_1(t_{k+4})$, ... and a series of second measurement signals $I_2(t_{k+1})$, $I_2(t_{k+3})$, $I_2(t_{k+5})$, ... are serially produced at successive moments $t_k$, $t_{k+1}$, $t_{k+2}$, ... in time, with k representing an integer number. The data evaluation unit is arranged to infer a particle number concentration N and an average particle diameter $d_{p,av}$ of the size distribution of electrically-charged airborne particles at each moment $t_k$, $t_{k+1}$, $t_{k+2}$, ... when either a first measurement signal $I_1$ or a second measurement signal $I_2$ is produced.

Further, a key aspect of the present invention lies in checking at the time $t=t_k$ with only the previous most recently inferred value $d_{p,av}(t_{k-1})$ at time $t_{k-1}$ to find out whether the (provisionally) inferred value $d_{p,av}(t_k)$ on the basis of only the last measured set of sensor signals $I_1$ and $I_2$ (i.e on the basis of either the set $(I_1(t_k),I_2(t_{k-1}))$ or the set $(I_1(t_{k-1}),I_2(t_k))$, depending on whether at $t=t_k$ the sensor signal $I_1(t_k)$ is measured or the sensor signal $I_2(t_k)$) according to Eq. 2 differs by more than a pre-defined amount f (with f>1) or 1/f from $d_{p,av}(t_{k-1})$. If this is not the case, the final value $d_{p,av}(t_k)$ is set equal to the provisionally inferred value $d_{p,av}(t_k)$ inferred from either the measured signals $(I_1(t_{k-1}),I_2(t_k))$ or from $(I_2(t_{k-1}), I_1(t_k))$ according to Eq. 2 which is valid for the static situation wherein the air pollution characteristics remain reasonably constant over time. However, if this is the case, the provisionally obtained value $d_{p,av}(t_k)$ is rejected and the final value $d_{p,av}(t_k)$ is only allowed to differ from $d_{p,av}(t_{k-1})$ by a limited amount for 1/f depending on whether the provisionally determined $d_{p,av}(t_k)>d_{p,av}(t_{k-1})$ or whether the provisionally determined $d_{p,av}(t_k)<d_{p,av}(t_{k-1})$, respectively. On the basis of the then determined final value for $d_{p,av}(t_k)$, the value $N(t_k)$ is evaluated. This procedure is further illustrated by the algorithm described under "Detailed exempling embodiment" below.

According to an alternative embodiment of the present invention, the number of inferred data sets ($d_{p,av}$, N) during a certain time span is made as large as possible without compromising on the accuracy of the inferred data. This aspect of the invention is implemented by inferring a data set ($d_{p,av}(t_k)$, $N(t_k)$) at any time $t_k$ wherein either a sensor signal $I_1(t_k)$ or a sensor signal $I_2(t_k)$ is obtained. The determination is done according to the algorithm described below. Thus, the data set ($d_{p,av}(t_k),N(t_k)$) can be inferred from both the sensor signal set $(I_1(t_{k-1}),I_2(t_k))$ or from the set $(I_2(t_{k-1}),I_1(t_k))$.

Another key aspect of the invention is that the relative health risk associated with the exposure to the ultra fine particle pollution (which is proportional to the particle length concentration $L=N*d_{p,av}$) is also determined at each time $t_k$ wherein either a sensor signal $I_1(t_k)$ or a sensor signal $I_2(t_k)$ is obtained. This health risk at time $t_k$ is set proportional to either the sensor signal $I_1(t_k)$ or to the sensor signal $I_1(t_{k-1})$ dependent on whether the last value for $I_1$ was measured at $t_k$ or $t_{k-1}$, respectively. Thus, no averaging is involved in the determination of the health risk associated with exposure to UFP air pollution at any moment in time.

Detailed Exemplifying Embodiment

Without wishing to be bound by any specific procedure or theory, herein after an exemplifying method and embodiment of the device is explained in more detail. The evaluation unit 29 is arranged to infer the particle number concentration N and the average particle diameter $d_{p,av}$ of the size distribution of electrically-charged airborne particles in the sampled airflow that passes through the device. In essence, according to prior art described in WO WO2007/000710 A2, the basic sensor in FIG. 1a enables the evaluation of N, $d_{p,av}$ and L at $\phi=\phi^*$ according to $$N = S_N(I_1 - I_2) \quad \text{Eq. 6}$$

$$d_{p,av} = S_{dp}\frac{I_1}{I_1 - I_2} \quad \text{Eq. 7}$$

$$L = Nd_{p,av} = S_N S_{dp} I_1 \quad \text{Eq. 8}$$

provided that substantially stationary conditions exist with respect to the characteristics of the size distribution of electrically-charged airborne particles during the period of time wherein a pair of serially measured signals $I_1$ and $I_2$ are measured. $S_N$ and $S_{dp}$ represent calibrated or calculated constant proportionality factors.

In the present embodiment, to improve upon the accuracy of the inferred values for N and $d_{p,av}$ at a given value for L (which can be obtained from a measurement of only $I_1$ according to Eq. 3) when transient conditions exist, the following protocol is executed by the evaluation unit 29 during the entire history of measurements wherein a string of sensor current measurements $I_1(t_0)$, $I_2(t_1)$, $I_1(t_2)$, $I_2(t_3)$, ... $I_1(t_k)$, $I_2(t_{k+1})$, $I_1(t_{k+2})$, $I_2(t_{k+3})$, ...

is serially recorded at the times $t_0$, $t_1$, $t_2$, ....

The following parameters are now defined:

$d_{p,0}$, which is a pre-defined reference particle diameter, and which is preferably chosen such that 20 nm $\leq d_{p,0} \leq$ 100 nm, $I_{1,ref}$, which is a pre-defined reference measurement signal having a numerical magnitude that is preferably set to a value in the 0-10 fA range.

f, which is a pre-defined parameter larger than unity and preferably $1.001 \leq f \leq 1.1$.

Meaningful values for multiple sets of results ($d_{p,av}(t_1)$, $N(t_1)$, $L(t_1)$), ($d_{p,av}(t_2)$, $N(t_2)$, $L(t_2)$), ($d_{p,av}(t_3)$, $N(t_3)$, $L(t_3)$), ... in the course of time can now be obtained through the following exemplary procedure that accounts and explicitly corrects for all kinds of measurement inaccuracies.

The very first set of measurements ($I_1(t_0)$, $I_2(t_1)$) obtained immediately after switching on the sensor instrument results in an inferred set of data ($d_{p,av}(t_1)$, $N(t_1)$, $L(t_1)$) at $t=t_1$ according to the set of equations and conditions described below that can be executed in either the restricted mode or in the free mode. The choice whether to choose the free mode or the restricted mode must be made by the user of the device.

The restricted mode is preferably chosen when at $t=t_0$ and $t=t_1$ transient conditions are expected to exist with respect to the characteristics of the size distribution of airborne electrically-charged particles.

The free mode is preferably chosen in all other cases when the characteristics of the size distribution of airborne electrically-charged particles are expected to remain relatively constant at $t=t_0$ and $t=t_1$.

Restricted mode if $I_1(t_0) \leq I_2(t_1) \rightarrow d_{p,av}(t_1) = d_{p,0}$ $$N(t_1) = \frac{S_N S_{dp} I_1(t_0)}{d_{p,av}(t_1)}$$

$$L(t_1) = S_N S_{dp} I_1(t_0)$$

if $I_1(t_0) \leq I_{1,ref} \rightarrow d_{p,av}(t_1) = d_{p,0}$ $$N(t_1) = \frac{S_N S_{dp} I_1(t_0)}{d_{p,av}(t_1)}$$

$$L(t_1) = S_N S_{dp} I_1(t_0)$$

-continued else if $\dfrac{1}{f} \leq \dfrac{S_{dp}I_1(t_0)}{(I_1(t_0)-I_2(t_1))d_{p,0}} \leq f \;\rightarrow\; d_{p,av}(t_1) = \dfrac{S_{dp}I_1(t_0)}{(I_1(t_0)-I_2(t_1))}$ $N(t_1) = S_N(I_1(t_0) - I_2(t_1))$ $L(t_1) = S_N S_{dp} I_1(t_0)$ if $\dfrac{S_{dp}I_1(t_0)}{(I_1(t_0)-I_2(t_1))d_{p,0}} < \dfrac{1}{f} \;\rightarrow\; d_{p,av}(t_1) = \dfrac{1}{f} d_{p,0}$ $N(t_1) = \dfrac{S_N S_{dp} I_1(t_0)}{d_{p,av}(t_1)}$ $L(t_1) = S_N S_{dp} I_1(t_0)$ if $\dfrac{S_{dp}I_1(t_0)}{(I_1(t_0)-I_2(t_1))d_{p,0}} > f \;\rightarrow\; d_{p,av}(t_1) = f d_{p,0}$ $N(t_1) = \dfrac{S_N S_{dp} I_1(t_0)}{d_{p,av}(t_1)}$ $L(t_1) = S_N S_{dp} I_1(t_0)$ The restricted mode for the first measurement always results in a first set of results $(d_{p,av}(t_1), N_1(t_1), L(t_1))$ as long as $I_1(t_0) > 0$ fA.

Free mode if $I_1(t_0) \leq I_2(t_1) \;\rightarrow\; d_{p,av}(t_1) = d_{p,0}$ $N(t_1) = \dfrac{S_N S_{dp} I_1(t_0)}{d_{p,av}(t_1)}$ $L(t_1) = S_N S_{dp} I_1(t_0)$ if $I_1(t_0) \leq I_{1,ref} \;\rightarrow\; d_{p,av}(t_1) = d_{p,0}$ $N(t_1) = \dfrac{S_N S_{dp} I_1(t_0)}{d_{p,av}(t_1)}$ $L(t_1) = S_N S_{dp} I_1(t_0)$ else $d_{p,av}(t_1) = \dfrac{S_{dp}I_1(t_0)}{(I_1(t_0) - I_2(t_1))}$ $N(t_1) = S_N(I_1(t_0) - I_2(t_1))$ $L(t_1) = S_N S_{dp} I_1(t_0)$ This always results in a first set of results $(d_{p,av}(t_1), N_1(t_1), L(t_1))$ as long as $I_1(t_0) > 0$ fA.

For the second and subsequent sets of inferred data for $N$, $d_{p,av}$ and $L$, the algorithm is implemented according to the restricted mode as described below:

The second set of inferred data $(d_{p,av}(t_2), N(t_2), L(t_2))$ is obtained from the sensor signals $(I_1(t_2), I_2(t_1))$ according to the set of equations and conditions:

if $I_1(t_2) \leq I_2(t_1) \;\rightarrow\; d_{p,av}(t_2) = d_{p,av}(t_1)$ $N(t_2) = \dfrac{S_N S_{dp} I_1(t_2)}{d_{p,av}(t_2)}$ $L(t_2) = S_N S_{dp} I_1(t_2)$ if $I_1(t_2) \leq I_{1,ref} \;\rightarrow\; d_{p,av}(t_2) = d_{p,av}(t_1)$ $N(t_2) = \dfrac{S_N S_{dp} I_1(t_2)}{d_{p,av}(t_2)}$ $L(t_2) = S_N S_{dp} I_1(t_2)$ else if $\dfrac{1}{f} \leq \dfrac{S_{dp}I_1(t_2)}{(I_1(t_2)-I_2(t_1))d_{p,av}(t_1)} \leq f \;\rightarrow\; d_{p,av}(t_2) = \dfrac{S_{dp}I_1(t_2)}{(I_1(t_2)-I_2(t_1))}$ $N(t_2) = S_N(I_1(t_2) - I_2(t_1))$ $L(t_2) = S_N S_{dp} I_1(t_2)$ if $\dfrac{S_{dp}I_1(t_2)}{(I_1(t_2)-I_2(t_1))d_{p,av}(t_1)} < \dfrac{1}{f} \;\rightarrow\; d_{p,av}(t_2) = \dfrac{1}{f} d_{p,av}(t_1)$ $N(t_2) = \dfrac{S_N S_{dp} I_1(t_2)}{d_{p,av}(t_2)}$ $L(t_2) = S_N S_{dp} I_1(t_2)$ if $\dfrac{S_{dp}I_1(t_2)}{(I_1(t_2)-I_2(t_1))d_{p,av}(t_1)} > f \;\rightarrow\; d_{p,av}(t_2) = f d_{p,av}(t_1)$ $N(t_2) = \dfrac{S_N S_{dp} I_1(t_2)}{d_{p,av}(t_2)}$ $L(t_2) = S_N S_{dp} I_1(t_2)$ More in general, when at $t=t_k$ ($k>1$) a sensor signal $I_1(t_k)$ is measured, the data $d_{p,av}(t_k)$, $N(t_k)$, and $L(t_k)$ are obtained according to if $I_1(t_k) \leq I_2(t_{k-1}) \;\rightarrow\; d_{p,av}(t_k) = d_{p,av}(t_{k-1})$ $N(t_k) = \dfrac{S_N S_{dp} I_1(t_k)}{d_{p,av}(t_k)}$ $L(t_k) = S_N S_{dp} I_1(t_k)$ if $I_1(t_k) \leq I_{1,ref} \;\rightarrow\; d_{p,av}(t_k) = d_{p,av}(t_{k-1})$ $N(t_k) = \dfrac{S_N S_{dp} I_1(t_k)}{d_{p,av}(t_k)}$ $L(t_k) = S_N S_{dp} I_1(t_k)$ else if $\dfrac{1}{f} \leq \dfrac{S_{dp}I_1(t_k)}{(I_1(t_k)-I_2(t_{k-1}))d_{p,av}(t_{k-1})} \leq f \;\rightarrow\; d_{p,av}(t_k) = \dfrac{S_{dp}I_1(t_k)}{(I_1(t_k)-I_2(t_{k-1}))}$ $N(t_k) = S_N(I_1(t_k) - I_2(t_{k-1}))$ $L(t_k) = S_N S_{dp} I_1(t_k)$ if $\dfrac{S_{dp}I_1(t_k)}{(I_1(t_k)-I_2(t_{k-1}))d_{p,av}(t_{k-1})} < \dfrac{1}{f} \;\rightarrow\; d_{p,av}(t_k) = \dfrac{1}{f} d_{p,av}(t_{k-1})$ $N(t_k) = \dfrac{S_N S_{dp} I_1(t_k)}{d_{p,av}(t_k)}$ $L(t_k) = S_N S_{dp} I_1(t_k)$ if $\dfrac{S_{dp}I_1(t_k)}{(I_1(t_k)-I_2(t_{k-1}))d_{p,av}(t_{k-1})} > f \;\rightarrow\; d_{p,av}(t_k) = f d_{p,av}(t_{k-1})$ $N(t_k) = \dfrac{S_N S_{dp} I_1(t_k)}{d_{p,av}(t_k)}$ $L(t_k) = S_N S_{dp} I_1(t_k)$ Alternatively, when at $t=t_k$ a sensor signal $I_2(t_k)$ is measured, the data $d_{p,av}(t_k)$ and $N(t_k)$ are obtained according to $$\text{if } I_1(t_{k-1}) \le I_2(t_k) \rightarrow d_{p,av}(t_k) = d_{p,av}(t_{k-1})$$
$$N(t_k) = \frac{S_N S_{dp} I_1(t_{k-1})}{d_{p,av}(t_k)}$$
$$L(t_k) = S_N S_{dp} I_1(t_{k-1})$$

$$\text{if } I_1(t_{k-1}) \le I_{1,ref} \rightarrow d_{p,av}(t_k) = d_{p,av}(t_{k-1})$$
$$N(t_k) = \frac{S_N S_{dp} I_1(t_{k-1})}{d_{p,av}(t_k)}$$
$$L(t_k) = S_N S_{dp} I_1(t_{k-1})$$

else $$\text{if } \frac{1}{f} \le \frac{S_{dp} I_1(t_{k-1})}{(I_1(t_{k-1}) - I_2(t_k)) d_{p,av}(t_{k-1})} \le f \rightarrow d_{p,av}(t_k) = \frac{S_{dp} I_1(t_{k-1})}{(I_1(t_{k-1}) - I_2(t_k))}$$
$$N(t_k) = S_N (I_1(t_{k-1}) - I_2(t_k))$$
$$L(t_k) = S_N S_{dp} I_1(t_{k-1})$$

$$\text{if } \frac{S_{dp} I_1(t_{k-1})}{(I_1(t_{k-1}) - I_2(t_k)) d_{p,av}(t_{k-1})} < \frac{1}{f} \rightarrow d_{p,av}(t_k) = \frac{1}{f} d_{p,av}(t_{k-1})$$
$$N(t_k) = \frac{S_N S_{dp} I_1(t_{k-1})}{d_{p,av}(t_k)}$$
$$L(t_k) = S_N S_{dp} I_1(t_{k-1})$$

$$\text{if } \frac{S_{dp} I_1(t_{k-1})}{(I_1(t_{k-1}) - I_2(t_k)) d_{p,av}(t_{k-1})} > f \rightarrow d_{p,av}(t_k) = f d_{p,av}(t_{k-1})$$
$$N(t_k) = \frac{S_N S_{dp} I_1(t_{k-1})}{d_{p,av}(t_k)}$$
$$L(t_k) = S_N S_{dp} I_1(t_{k-1})$$

The above procedure much reduces random scatter in the inferred values $d_{p,av}$ during a certain period of time and simultaneously makes inferred values for N more reliable, while remaining uncompromising is as far the evaluation of the exposure associated risk L is concerned.

Examples of applications in which embodiments of a device in accordance with the present invention are suitable are e.g. environmental monitoring, occupational exposure measurements, research instrumentation and particle filter testing instrumentation.

While the invention has been illustrated and described in detail in the drawings and foregoing description, such illustration and description are to be considered illustrative or exemplary and not restrictive; the invention is not limited to the disclosed embodiments. Variations to the disclosed embodiments can be understood and effected by those skilled in the art in practicing the claimed invention, from a study of the drawings, the disclosure, and the appended claims. In the claims, the word "comprising" does not exclude other elements, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A device for characterizing the evolution over time of a size distribution of electrically-charged airborne particles in an airflow, comprising:

an air inlet for entry of airborne particles in an airflow, a particle charging unit arranged to create electrically-charged airborne particles by electrically charging airborne particles having a size distribution entering the device, a concentration variation section to cause a variation of the concentration of electrically-charged particles between at least a first concentration level and a second concentration level during at least one time interval, a particle sensing section to produce a first measurement signal corresponding with the first concentration level, and a second measurement signal corresponding with the second concentration level, and a data evaluation unit being arranged to infer a particle number concentration and an average particle diameter of the size distribution of electrically-charged airborne particles from the first measurement signal and the second measurement signal and a reference particle diameter, wherein the data evaluation unit rejects the inferred average particle diameter when the change of the inferred average particle diameter with respect to the reference particle diameter exceeds a set maximum change.

2. The device according to claim 1, wherein the particle number concentration is inferred on the basis of the first measurement signal, the second measurement signal, and the inferred average particle diameter of the size distribution of electrically-charged airborne particles.

3. The device according to claim 1, wherein the concentration variation section is an electrical precipitation unit capable of electrically precipitating at least part of the size distribution of electrically-charged airborne particles during at least one time interval.

4. The device according to claim 1, wherein the first concentration level is substantially the same as the concentration level of the created electrically-charged airborne particles at the particle charging unit.

5. The device according to claim 1, wherein the reference particle diameter is a pre-defined particle diameter.

6. The device according to claim 5, wherein the pre-defined particle diameter is preferably set at a value within the 20-100 nm size range.

7. The device according to claim 1, wherein the reference particle diameter is a previously inferred average particle diameter.

8. The device according to claim 1, wherein the inferred average particle diameter is taken to be equal to the reference particle diameter when the first measurement signal is smaller than or equal to the second measurement signal.

9. The device according to claim 1, wherein the inferred average particle diameter is taken to be equal to the reference particle diameter when the first measurement signal is smaller than or equal to a pre-defined reference signal.

10. The device according to claim 1, wherein the mathematical product of the inferred average particle diameter and the inferred particle number concentration is set to be proportional to the first measurement signal.

11. The device according to claim 1, wherein the said set maximum change depends on the magnitude of at least one of the first and second measurements signals, respectively.

12. The device according to claim 1, wherein a series of first measurement signals and a series of second measurement signals are serially produced at successive moments in time, and wherein the data evaluation unit is arranged to infer a particle number concentration and an average particle diameter of the size distribution of electrically-charged airborne particles at each of the successive moments in time when either a first measurement signal or a second measurement signal is produced.

13. The device according to claim 1, wherein the device is arranged for measuring the evolution over time of the characteristics of a size distribution of electrically-charged airborne particles, which are predominantly electrically-charged ultrafine particles with a diameter in the 5-500 nm size range, more preferably in the 10-300 nm size range.

* * * * *